United States Patent [19]
Hedengren et al.

[11] Patent Number: 5,841,277
[45] Date of Patent: Nov. 24, 1998

[54] HAND-HOLDABLE PROBE HAVING A FLEXIBLE EDDY CURRENT SENSOR

[75] Inventors: Kristina Helena Valborg Hedengren; John David Young, both of Schenectady, N.Y.; Thomas Burrows Hewton; Carl Granger, Jr., both of West Chester, Ohio

[73] Assignee: General Electric Company, Schenectady, N.Y.

[21] Appl. No.: 803,612

[22] Filed: Feb. 21, 1997

Related U.S. Application Data

[60] Provisional application No. 60/022,406 Jul. 30, 1996.
[51] Int. Cl.$^6$ .......................... G01R 33/12; G01N 27/82; G01N 27/72
[52] U.S. Cl. .......................... 324/240; 324/237; 324/238; 324/262
[58] Field of Search .................................. 324/219, 220, 324/226, 228, 234, 236, 237, 238, 239, 240, 241, 242, 243, 262

[56] References Cited

U.S. PATENT DOCUMENTS

| | | | |
|---|---|---|---|
| 3,523,241 | 8/1970 | Barton | 324/262 |
| 4,543,528 | 9/1985 | Baraona | 324/243 |
| 5,182,513 | 1/1993 | Young et al. | |
| 5,262,722 | 11/1993 | Hedengren et al. | |
| 5,315,234 | 5/1994 | Sutton, Jr. et al. | |
| 5,345,514 | 9/1994 | Mahdavieh et al. | |
| 5,371,462 | 12/1994 | Hedengren et al. | |
| 5,389,876 | 2/1995 | Hedengren et al. | |
| 5,442,286 | 8/1995 | Sutton, Jr. et al. | |

Primary Examiner—Walter E. Snow
Attorney, Agent, or Firm—Douglas E. Erickson; Marvin Snyder

[57] ABSTRACT

A probe, such as an eddy current probe, which can be moved by hand to a surface to be tested. A toroidal-shaped first resilient member contacts the bottom face of a support member. An elastic membrane extends over the bore of the first resilient member, contacts the bottom lateral surface of the first resilient member, and is unattached to the radially-inward-facing surface of the first resilient member. A more elastic, second resilient member is placed in the bore, is unattached to the first resilient member, and contacts the bottom surface of the elastic membrane. A flexible, surface-conformable, eddy current sensing coil overlies a portion of the bottom side of the second resilient member. More broadly stated, the probe includes first apparatus, for providing a stand-off distance between the support member and the surface, and second apparatus, which includes a flexible sensor (such as an eddy-current sensing coil), for providing a predetermined force to the surface, the predetermined force being essentially decoupled from any force applied to the surface by the first apparatus.

8 Claims, 4 Drawing Sheets

HAND-HOLDABLE PROBE HAVING A FLEXIBLE EDDY CURRENT SENSOR

This application claims priority of a Provisional Application entitled "Hand-Held Probe Incorporating A Flexible Circuit Eddy Current Sensor" by Thadd C. Patton et al., Ser. No. 60/022,406 filed Jul. 30, 1996.

FIELD OF THE INVENTION

The present invention relates generally to sensing systems (such as an eddy current inspection system for detecting flaws in electrically conductive articles), and more particularly to a hand-holdable probe for a sensing system (such as an eddy current probe for an eddy current inspection system).

BACKGROUND OF THE INVENTION

It is well known in the art to use eddy current inspection systems which use nondestructive eddy currents to test for the presence of surface, or near surface, flaws or defects in electrically conductive objects. Such inspection systems typically employ circular eddy current probes each having an eddy-current driving coil and an eddy-current sensing coil which may or may not be the same coil. However, an eddy current probe is known which includes numerous, individually sensed, generally-identical, flexible eddy-current sensing coils in a multiple row and multiple off-set column rectangular array with each sensing coil having the shape of a rectangle with a length-to-width ratio of generally two. Optimum efficiency of the eddy-current sensing coils occurs when the sensors are placed in direct contact with a part under inspection. A uniform pressure is necessary to provide consistent and repeatable inspection results with sufficient signal-to-noise ratio. Hence, curved surfaces (i.e., smoothly varying concave and convex surfaces including radius corners) present a challenge to eddy-current flaw detection systems. A known solution employs compressed gas of controlled pressure against the back of a flexible eddy-current sensing coil array in an eddy current probe which is under the control of a multi-axis mechanical control system to precisely manipulate the probe over a part under inspection. Similar problems would occur with other sensing system probes including, without limitation, a ferroelectric polymer such as poly(vinylidene fluoride) for ultrasonic testing, two capacitor plates for pressure testing, a thermocouple, and the like, and combinations thereof, as can be appreciated by those skilled in the art.

What is needed is a sensing system probe (such as an eddy-current-type sensing system probe) which is inexpensive, which can be hand held, which is self-contained to deliver a uniform pressure against a straight or smoothly-curved surface, and which essentially has the same or better sensitivity than a conventional probe connected to a mechanical positional control system.

SUMMARY OF THE INVENTION

Broadly described, the probe of the invention includes a support member movable proximate a surface of an object to be tested for flaws, first apparatus for providing a stand-off distance between the support member and the surface when the support member is moved near the surface, and second apparatus for providing a predetermined force to the surface when the first apparatus contacts the surface. The first apparatus contacts the surface and the support member when the support member is moved near the surface. The entire second apparatus is located near the support member and moves near the surface when the first apparatus contacts the surface. The predetermined force is generally decoupled from any force applied to the surface by the first apparatus when the first apparatus contacts the surface. The second apparatus includes a flexible sensor located near the surface when the first apparatus contacts the surface.

Several benefits and advantages are derived from the invention. The probe of the invention allows an operator to hold the probe in hand and allows the probe to provide an essentially constant pressure to the back of the flexible sensor which is generally decoupled from the variable pressure the operator uses to apply the probe against, and move the probe along, the surface under inspection all without the need for expensive multi-axis mechanical control systems and cumbersome compressed gas delivery apparatus.

DETAILED DESCRIPTION OF THE INVENTION

Figure 1:
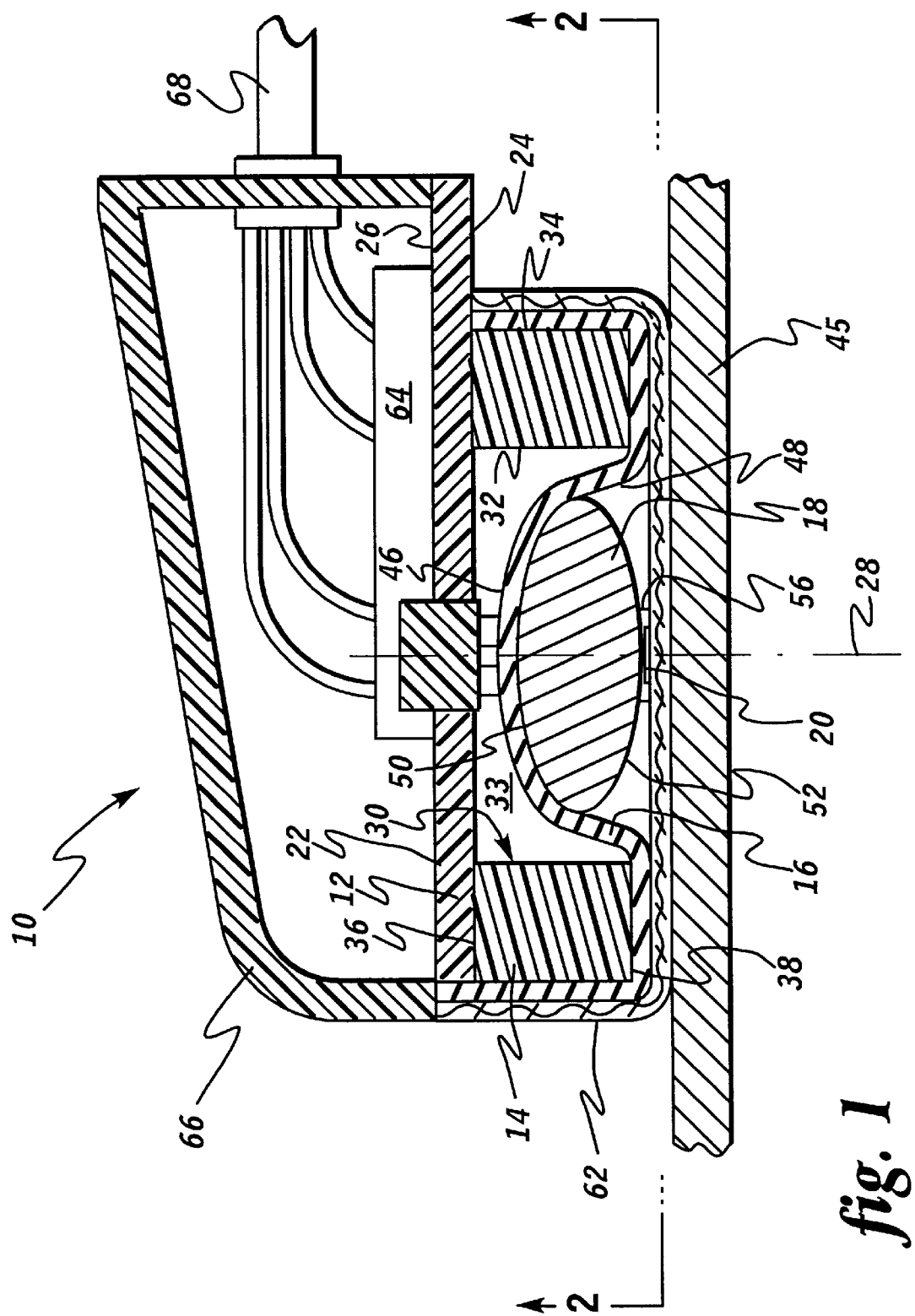
FIG. 1 is a schematic cross-sectional side view of a first preferred embodiment of an eddy-current-type sensing system probe of the invention including a first preferred embodiment of the first resilient member.
Figure 2:
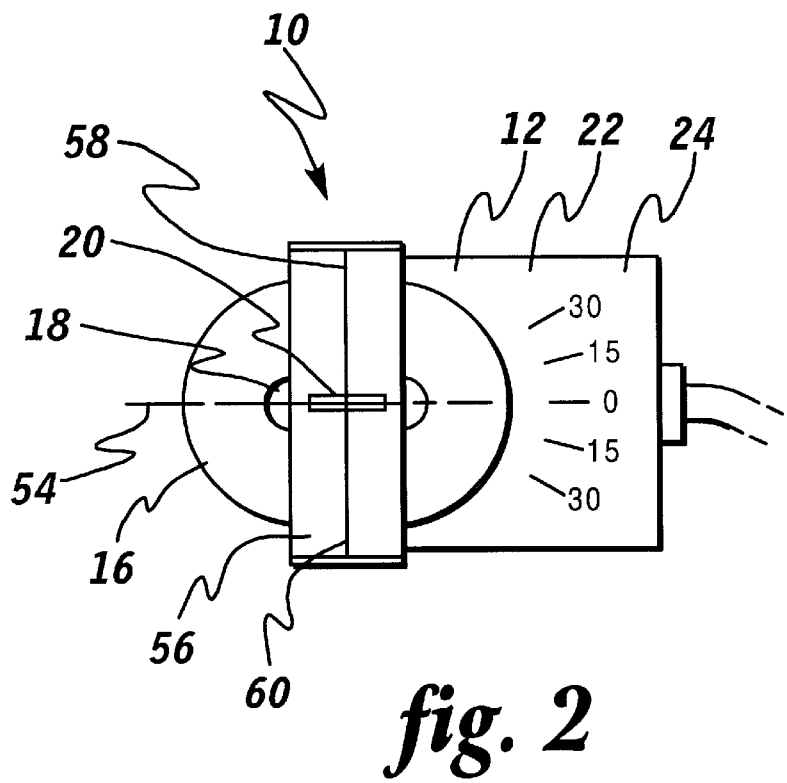
FIG. 2 is a bottom view of the eddy current probe of FIG. 1 taken along lines 2—2 of FIG. 1.

Referring now to the drawings, wherein like reference characters designate like or corresponding parts, FIGS. 1 and 2 show a first preferred embodiment of the eddy-current-type sensing system probe 10 of the invention. It is noted that an eddy current inspection system processes and displays signals from the eddy current probe 10, the processing and displaying of such signals being well known in the art and not forming a part of the present invention. The eddy current probe 10 of the invention includes a support member 12, a generally-toroidal-shaped first resilient member 14, an elastic membrane 16, a second resilient member 18, and a flexible eddy-current sensing coil 20. Typically, the probe 10 also includes a flexible eddy-current driving coil (omitted from the figures for clarity), as can be appreciated by those skilled in the art.

The support member 12 preferably is a plastic base plate 22 having opposing first and second faces 24 and 26. However, the support member 12 may have any shape. A preferred material for the support 12 is plastic.

The generally-toroidal-shaped first resilient member 14 has a first coefficient of elasticity, a generally longitudinal axis 28, and an exterior surface 30. The exterior surface 30 includes a generally radially-inward-facing portion 32 surrounding a bore 33, a generally radially-outward-facing portion 34, and generally opposite-facing first and second lateral portions 36 and 38 each connected to the radiallyinward-facing portion 32 and the radially-outward-facing portion 34. The first lateral portion 36 contacts the support member 12. Preferably, the first lateral portion 36 of the exterior surface 30 of the first resilient member 14 contacts and is attached to the first face 24 of the base plate 22. In a first preferred embodiment shown in FIG. 1, the first resilient member 14 is a single monolithic ring of resilient material such as, but not limited to, RTV (room temperature vulcanizing) silicone.

Figure 3:
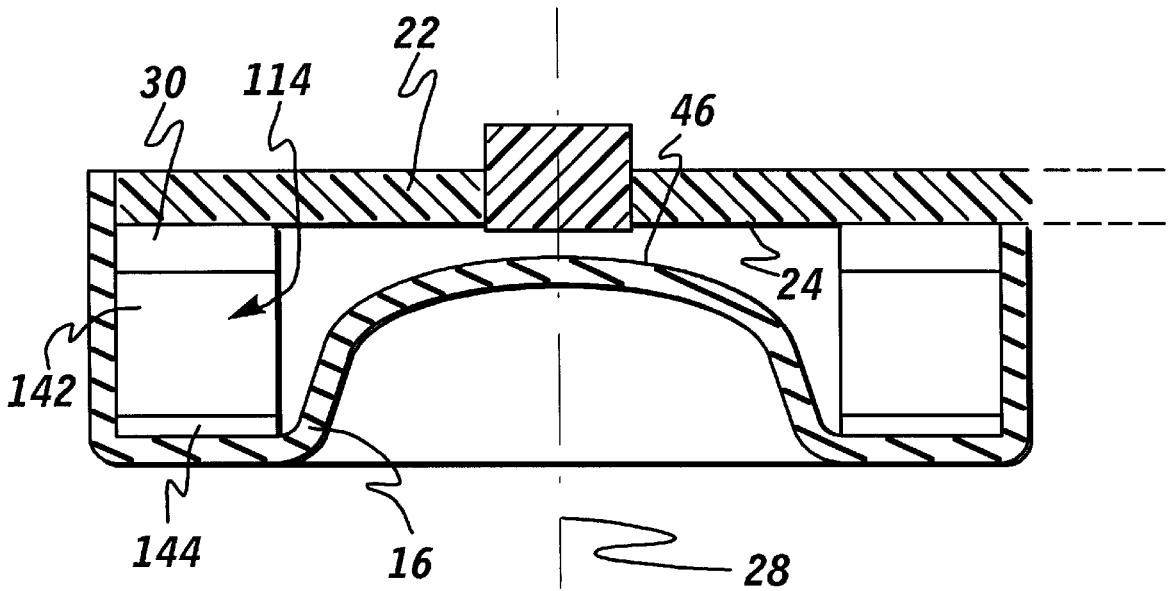
FIG. 3 is a schematic cross-sectional side view of a second preferred embodiment of the first resilient member (with cross hatching omitted for clarity) and adjacent members of the eddy current probe of the invention.

In a second preferred embodiment shown in FIG. 3, the first resilient member 114 comprises: a gel ring 140 generally coaxially aligned with the longitudinal axis 28 and attached to the first face 24 of the base plate 22; a foam ring 142 generally coaxially aligned with the longitudinal axis 28 and longitudinally attached to the gel ring 140; and an annular rubber contact shield 144 generally coaxially aligned with the longitudinal axis 28 and longitudinally attached to the foam ring 142. The foam ring 142 is longitudinally disposed between the gel ring 140 and the annular rubber contact shield 144. It is noted that the gel ring 140, the foam ring 142, and the annular rubber contact shield 144 are generally concentric. Preferably, the gel ring 140 consists essentially of RTV silicone, the foam ring 142 consists essentially of neoprene sponge rubber, and the annular rubber contact shield 144 consists essentially of foam rubber. The annular rubber contact shield 144 provides wear resistance, the gel ring 140 (which is always more elastic than the foam ring 142) allows the first resilient member 114 to better conform to the surface 45 (shown in FIG. 1) being tested, and the foam ring 142 provides the basic mechanical support for the resilient stand-off distance of the base plate 22 from the surface 45 being tested.

Figure 4:
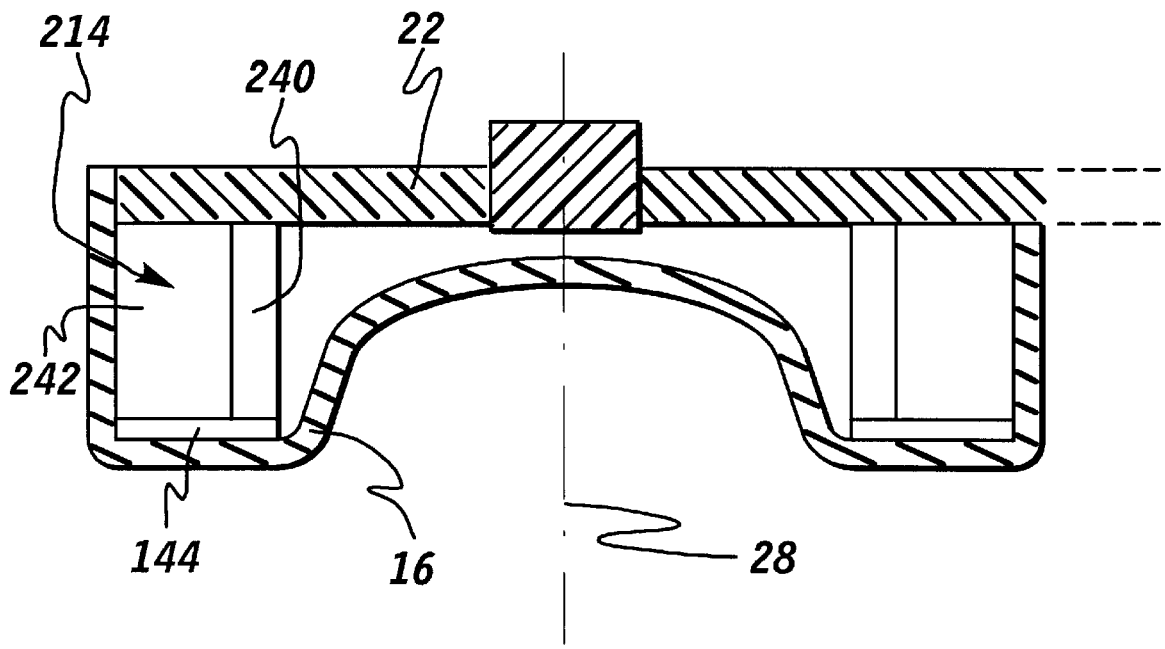
FIG. 4 is a view as in FIG. 3 but of a third preferred embodiment of the first resilient member and adjacent members of the probe of the invention.

In a third preferred embodiment, the geometry of the gel ring 240 and the foam ring 242, which together with the annular rubber contact shield 144 comprise the first resilient member 214, is rearranged as shown in FIG. 4. Here, the foam ring 242 is generally coaxially aligned with the longitudinal axis 28 and radially attached to the gel ring 240. The inner diameter of the foam ring 242 is generally equal to the outer diameter of the gel ring 240. Such design will better conform to a surface 45 being tested which has a concave shape.

Figure 5:
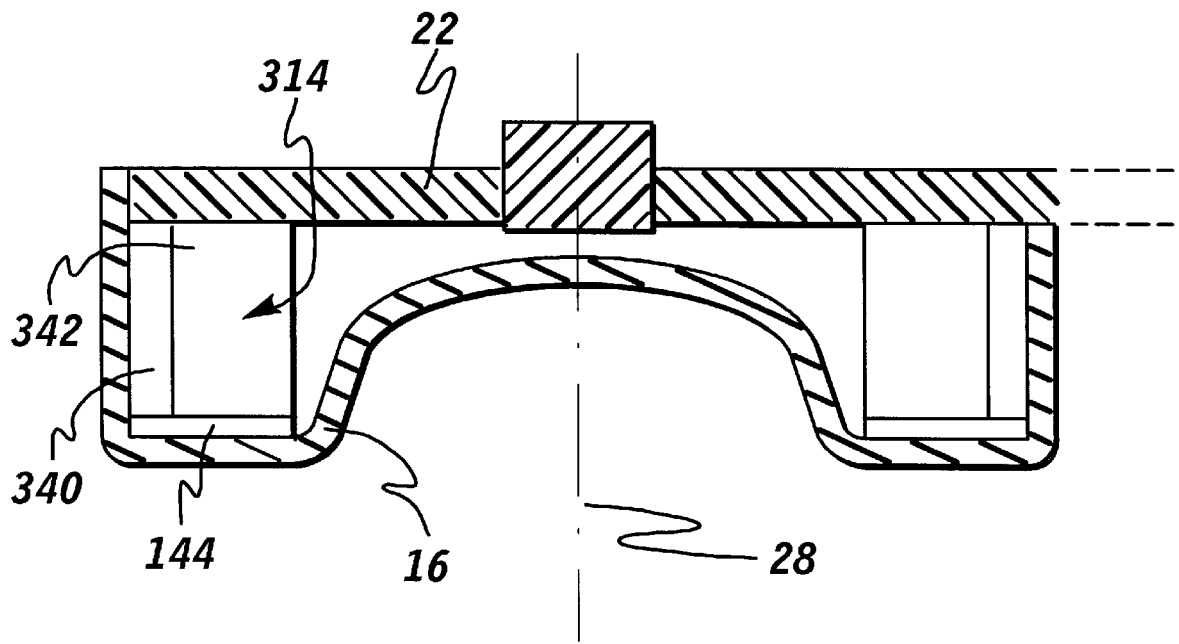
FIG. 5 is a view as in FIG. 3 but of a fourth preferred embodiment of the first resilient member and adjacent members of the probe of the invention.

In a fourth preferred embodiment, the geometry of the gel ring 340 and the foam ring 342, which together with the annular rubber contact shield 144 comprise the first resilient member 314, is rearranged as shown in FIG. 5. The outer diameter of the foam ring 342 is generally equal to the inner diameter of the gel ring 340. Such design will better conform to a surface 45 being tested which has a convex shape.

The elastic membrane 16 extends over generally the entire bore 33 and has opposing first and second surfaces 46 and 48. The first surface 46 contacts the second lateral portion 38 of the exterior surface 30 of the first resilient member 14 and is unattached to the radially-inwardly-facing portion 32 of the exterior surface 30 of the first resilient member 14. In an exemplary construction, the first surface 46 of the elastic membrane 16 is attached to the second lateral portion 38 of the exterior surface 30 of the first resilient member 14. It is desired that the elastic membrane 16 is also attached to the base plate 22. Preferably, the elastic membrane 16 consists essentially of latex rubber. When the first resilient member 114 includes the annular rubber contact shield 144, as shown in FIG. 3, the exemplary construction has the first surface 46 of the elastic membrane 16 attached to the annular rubber contact shield 144.

The second resilient member 18 has a second coefficient of elasticity which is greater than the first coefficient of elasticity of the first resilient member 14. The second resilient member 18 is disposed in the bore 33, is unattached to the first resilient member 14, and has generally opposing first and second sides 50 and 52. It is noted that the first side 50 of the second resilient member 18 contacts the second surface 48 of the elastic membrane 16.

The flexible eddy-current sensing coil 20 overlies a portion of the second side 52 of the second resilient member 18. Preferably, the eddy-current sensing coil 20 is the only eddy-current sensing coil overlying the second side 52 of the second resilient member 18. In a preferred construction, the eddy-current sensing coil 20 has a generally rectangular shape with a lengthwise axis 54 and a length-to-width ratio of at least three (and preferably of at least six). It is noted that the preferred narrow-rectangular-shaped single eddy-current sensing coil 20 provides the same inspection coverage as known multi-coil systems. With such preferred construction, it is desired that the second resilient member 18 have a generally ellipsoidal shape having a major axis aligned generally parallel to the lengthwise axis 54 of the eddy-current sensing coil 20. However, the eddy-current sensing coil 20 may have any geometry or even any combination of spaced-apart, electrically-connected subcoils.

Preferably, the eddy-current sensing coil 20 is rotatably attached to the base plate 22 and is rotatable generally about the longitudinal axis 28. With a rotatable eddy-current sensing coil 20, it is desired that the eddy current probe 10 also include means for measuring the angle of rotation of the lengthwise axis 54 of the eddy-current sensing coil 20 about the longitudinal axis 28 with respect to a reference direction which is fixed with respect to the base plate 22. Preferably, such means include angle markings on the first face 24 of the base plate 22 as shown in FIG. 2. Other such means include a digital readout of such angles, and the like, as is within the skill of the artisan. Applicants have found that some flaws are more easily detectable with the eddy-current sensing coil 20 being offset at an angle from the direction of travel of the eddy current probe 10 over the surface 45 being tested.

In a preferred embodiment, the eddy current probe 10 also includes a flexible polyimide film 56 containing flexible electric leads 58 and 60. The eddy-current sensing coil 20 is disposed in the polyimide film 56 and is connected to the electric leads 58 and 60. In a desired construction, the polyimide film 56 is attached (and preferably rotatably attached) to the base plate 22.

In an exemplary enablement, the eddy current probe 10 further includes a polyamide mesh fabric 62 overlying the polyimide film 56. The polyamide mesh fabric 62 is what actually contacts the surface 45 being tested. The purpose of the polyamide mesh fabric 62, which is easily replaceable, is to take the wear and tear of contact with the surface 45 being tested. It is noted that Teflon® tape can also be used for this purpose.

In a preferred construction, the eddy current probe 10 additionally includes a signal preamplifier 64 attached to the second face 26 of the base plate 22 and electrically connected to the eddy-current sensing coil 20. This inherently places the signal preamplifier 64 proximate the eddy-current sensing coil 20 as compared to conventional eddy-current inspection systems. The essentially co-location of the signal preamplifier 64 and the eddy-current sensing coil 20 improves the signal-to-noise level and hence improves flaw detection.

It is noted that the eddy current probe 10, described above, allows an operator to hold the probe 10 in hand and allows the probe to provide an essentially constant pressure to the back of the flexible eddy-current sensing coil 20 which is generally decoupled from the variable pressure the operator uses to apply the probe 10 against, and move the probe 10 along, the surface 45 under inspection. If desired, the probe 10 may be moved by a mechanical control system, but a preferred mode of operation is to move the probe 10 by hand. For stability, a jig may be used to guide the hand motion of the probe. FIG. 1 additionally shows a hand-conformable, plastic housing 66 covering the second face 26 of the base plate 22 and a cable 68 leading to the signal processing and image displaying portions of the eddy current inspection system, such other portions not shown in the figures.

From an appreciation of the particular embodiment of the eddy current probe 10 previously described, those skilled in the art will understand that the basic invention is more broadly described (in terms including previously described probe components) as a probe, such as the eddy-current-type sensing system probe 10, which includes a support member 12 movable proximate a surface 45 of an object to be tested for flaws and first means for providing a stand-off distance between the support member 12 and the surface 45 when the support member 12 is moved proximate the surface 45. The first means is in contact with the surface 45 and the support member 12 when the support member 12 is moved proximate the surface 45. Such proximate movement includes proximate movement directly towards the surface 45 and additionally preferably also includes proximate movement over the surface 45. Preferably, such first means includes the previously-described first resilient member 14, the overlying section of the previously described elastic membrane 16, and the overlying section of the previously described polyamide mesh fabric 62. Other such first means includes one or more arbitrary-shaped rigid and/or resilient block member (s), wherein resiliency may be provided by springs, gasses, liquids, elastomers, etc.

The more-broadly-described probe 10 also includes second means for providing a predetermined force to the surface 45 when the first means contacts the surface 45. The entire second means is disposed proximate the support member 12 and is moved proximate the surface 45 when the support member 12 is moved proximate the surface 45. The second means is in contact with the surface 45 when the first means contacts the surface 45. The predetermined force is generally decoupled from any force applied to the surface 45 by the first means when the first means contacts the surface 45. The second means includes a flexible sensor (such as the flexible eddy-current sensing coil 20) disposed proximate the surface 45 when the first means contacts the surface 45. Preferably, such second means also includes the previously described elastic membrane 16, the previously described second resilient member 18, the previously described flexible polyimide film 56, and the overlying portion of the previously described polyamide mesh fabric 62. Other such second means also includes a gas or liquid filled bladder, springs, elastomers, etc. disposed behind the eddy-current sensing coil 20, unattached to the first means, and attached to (or otherwise constrained to remain proximate to) the support member 12. As can be appreciated by those skilled in the art, such described second means provide a predetermined and generally constant force which is generally decoupled from any force applied to the surface 45 by the first means. The choice for the flexible sensor includes, without limitation, the previously-described eddy-current sensing coil 20, a ferroelectric polymer such as poly (vinylidene fluoride) for ultrasonic testing, two capacitor plates for pressure testing, a thermocouple, and the like, and combinations thereof, as can be appreciated by those skilled in the art. It is noted that the second means typically would also include a flexible driver (such as a flexible eddy-current driving coil) which, in some applications, may time-share the same structure as the sensor (such as a common transmit-receive transducer used in certain ultrasonic applications).

The following description is of a preferred embodiment of the more-broadly-described probe 10. The support member 12, first means, and second means together are hand hold-able. The second means provides the predetermined force solely by the movement of the support member 12 proximate the surface 45. The entire second means is disposed within the stand-off distance between the support member 12 and the surface 45 when the first means contacts the surface. The second means is more resilient than the first means.

Preferably, the eddy-current sensing coil 20 is the only eddy-current sensing coil included in the second means, and the eddy-current sensing coil 20 has a generally rectangular shape with a lengthwise axis 54 and a length-to-width ratio of at least three (and preferably of at least six). The eddy-current sensing coil 20 is rotatably attached to the support member 12. The probe 10 also includes third means for measuring the angle of rotation of the lengthwise axis 54 of the eddy-current sensing coil 20 with respect to a reference direction which is fixed with respect to the support member 12. Such third means is equivalent to the previously-described angle-measuring means. The probe 10 further includes a signal preamplifier 64 attached to the support member 12 and electrically connected to the eddy-current sensing coil 20.

Figure 6:
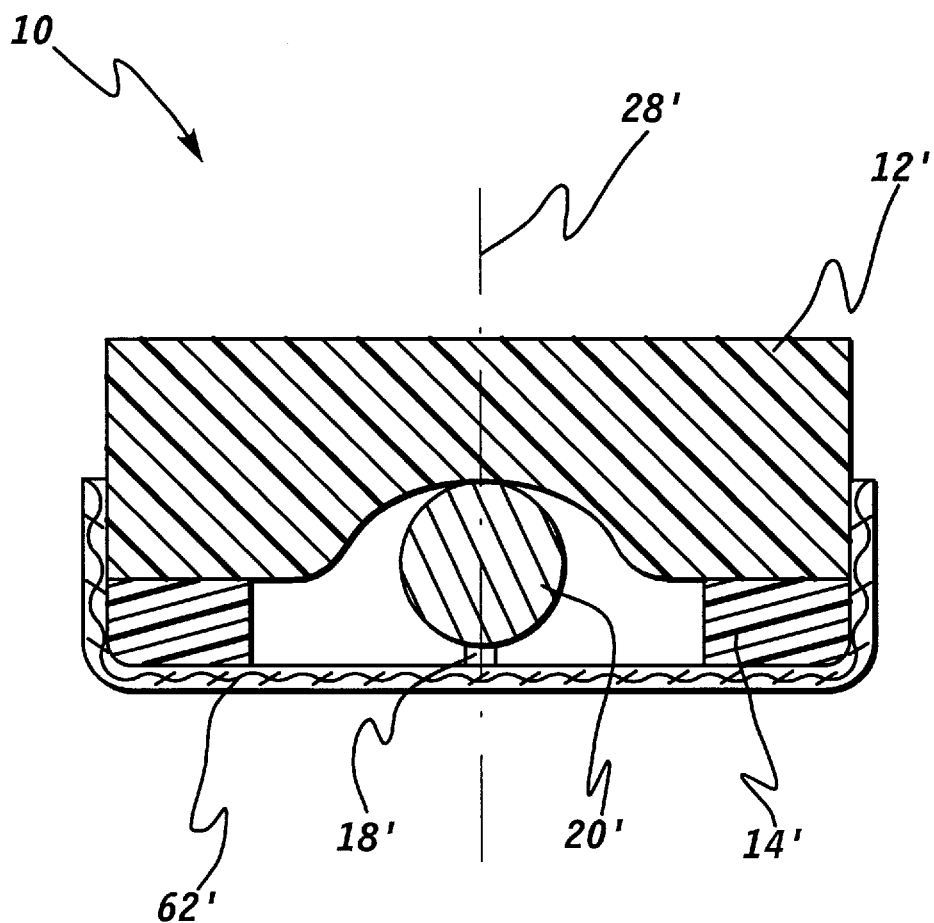
FIG. 6 is a view as in FIG. 1 but of a portion only of an alternate embodiment of the probe of the invention.

In an alternate embodiment shown in FIG. 6, the eddy current probe 10' includes: a support member 12'; a generally-toroidal-shaped first resilient member 14' having a generally longitudinal axis 28'; a second resilient member 18'; a flexible eddy-current sensing coil 20'; and a polyamide mesh fabric 62'.

The foregoing description of several preferred embodiments of the invention has been presented for purposes of illustration. It is not intended to be exhaustive or to limit the invention to the precise form disclosed, and obviously many modifications and variations are possible in light of the above teaching. It is intended that the scope of the invention be defined by the claims appended hereto.

We claim:

1. A probe comprising:
   a) a support member movable proximate a surface of an object to be tested for flaws;
   b) first means for providing a stand-off distance between said support member and said surface when said support member is moved proximate said surface, said first means in contact with said surface and said support member when said support member is moved proximate said surface; and
   c) second means for providing a predetermined force to said surface when said first means contacts said surface, the entire second means disposed proximate said support member and moved proximate said surface when said support member is moved proximate said surface, said second means in contact with said surface when said first means contacts said surface, said predetermined force generally decoupled from any force applied to said surface by said first means when said first means contacts said surface, and said second means including a flexible sensor disposed proximate said surface when said first means contacts said surface.

2. The probe of claim 1, wherein said support member, said first means, and said second means together are hand holdable.

3. The probe of claim 2, wherein said second means provides said predetermined force solely by the movement of said support member proximate said surface.

4. The probe of claim 3, wherein the entire second means is disposed within the stand-off distance between said support member and said surface when said first means contacts said surface.

5. The probe of claim 4, wherein said second means is more resilient than said first means.

6. The probe of claim 5, wherein said flexible sensor comprises a flexible eddy-current sensing coil having a generally rectangular shape with a lengthwise axis and a length-to-width ratio of at least three, and wherein said eddy-current sensing coil is the only eddy-current sensing coil included in said second means.

7. The probe of claim 1, wherein said flexible sensor comprises a flexible eddy-current sensing coil having a generally rectangular shape with a lengthwise axis and a length-to-width ratio of at least three, and wherein said eddy-current sensing coil is the only eddy-current sensing coil included in said second means.

8. The probe of claim 1, wherein said flexible sensor comprises a flexible eddy-current sensing coil, and also including a signal preamplifier attached to said support member and electrically connected to said eddy-current sensing coil.

* * * * *